(12) United States Patent
Ishinari et al.

(10) Patent No.: US 12,324,698 B2
(45) Date of Patent: Jun. 10, 2025

(54) RADIATION IMAGING SYSTEM, RADIATION IMAGING APPARATUS, CONTROL METHOD OF RADIATION IMAGING SYSTEM, AND NON-TRANSITORY COMPUTER-READABLE STORAGE MEDIUM

(71) Applicant: CANON KABUSHIKI KAISHA, Tokyo (JP)

(72) Inventors: Yutaka Ishinari, Kanagawa (JP); Tomoyuki Yagi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 218 days.

(21) Appl. No.: 18/046,829

(22) Filed: Oct. 14, 2022

(65) Prior Publication Data

US 2023/0119623 A1 Apr. 20, 2023

(30) Foreign Application Priority Data

Oct. 19, 2021 (JP) ................................. 2021-171149

(51) Int. Cl.
*A61B 6/00* (2024.01)
*A61B 6/46* (2024.01)
*G01N 23/04* (2018.01)

(52) U.S. Cl.
CPC .............. *A61B 6/542* (2013.01); *A61B 6/467* (2013.01); *A61B 6/548* (2013.01); *A61B 6/56* (2013.01);

(Continued)

(58) Field of Classification Search
CPC ......... A61B 6/542; A61B 6/467; A61B 6/548; A61B 6/56; A61B 6/563; A61B 6/566;
(Continued)

(56) References Cited

U.S. PATENT DOCUMENTS 9,301,727 B2 * 4/2016 Gonda ..................... A61B 6/56
10,610,187 B2 * 4/2020 Takeshima ............. A61B 6/542
(Continued)

FOREIGN PATENT DOCUMENTS

JP 2017094007 A 6/2017

*Primary Examiner* — Marcus H Taningco
(74) *Attorney, Agent, or Firm* — Canon U.S.A., Inc. IP Division

(57) ABSTRACT

A radiation imaging system comprising a radiation imaging apparatus configured to detect radiation emitted from a radiation source, an irradiation control apparatus configured to control the radiation source, a communication control apparatus configured to perform communication between the radiation imaging apparatus and the irradiation control apparatus, and a controller, is provided. The radiation imaging apparatus is configured to communicate with the communication control apparatus in accordance with a setting selected from a plurality of settings by the controller. The controller acquires a communication time for a predetermined communication amount between the radiation imaging apparatus and the communication control apparatus, and switches, in accordance with the communication time, the setting for communication of the radiation imaging apparatus with the communication control apparatus from a currently selected setting to another setting among the plurality of settings.

15 Claims, 6 Drawing Sheets

(52) U.S. Cl.
CPC .............. *A61B 6/563* (2013.01); *A61B 6/566* (2013.01); *G01N 23/04* (2013.01); *G01N 2223/306* (2013.01)

(58) Field of Classification Search
CPC .............. G01N 23/04; G01N 2223/306; G01N 2223/304; G01N 2223/612
See application file for complete search history.

(56) References Cited

U.S. PATENT DOCUMENTS

| | | | |
|---|---|---|---|
| 2012/0206233 A1* | 8/2012 | Kamiya ................. | A61B 6/566 340/2.1 |
| 2013/0208860 A1* | 8/2013 | Sugizaki .............. | A61B 6/4233 378/62 |
| 2018/0353150 A1* | 12/2018 | Takeshima ............... | A61B 6/56 |
| 2019/0290238 A1* | 9/2019 | Hara .................... | A61B 6/4494 |
| 2020/0008771 A1* | 1/2020 | Isogai ...................... | H05G 1/38 |

* cited by examiner

FIG. 1
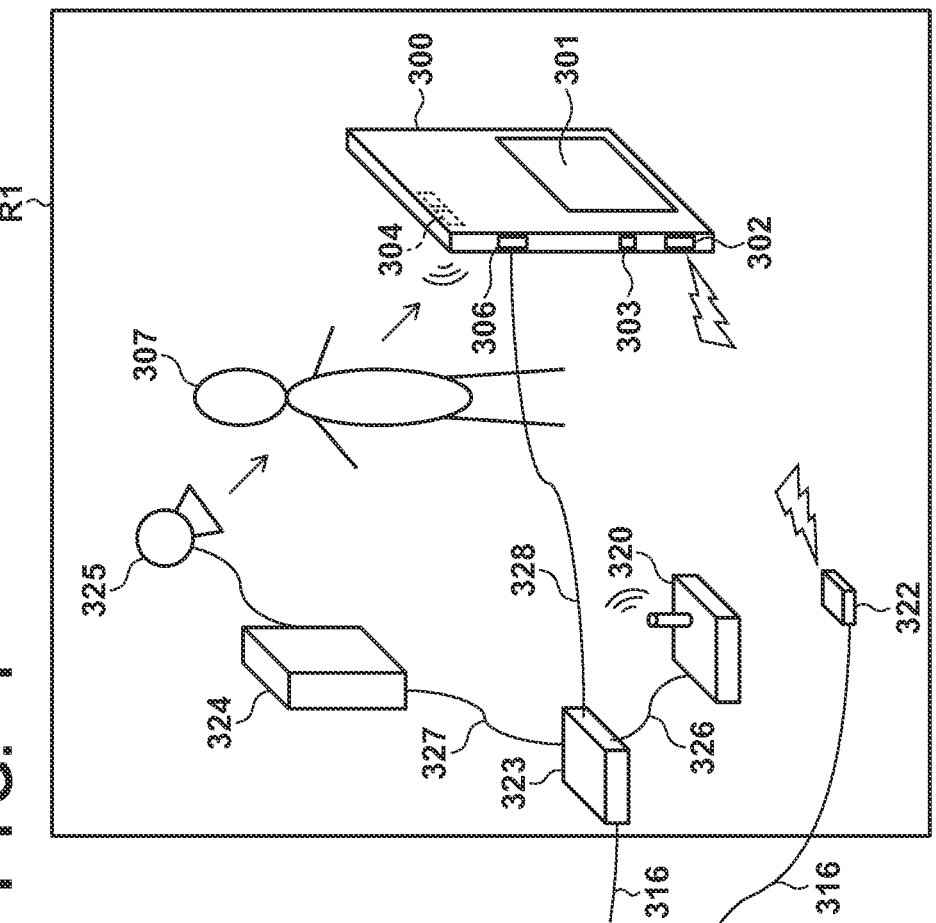
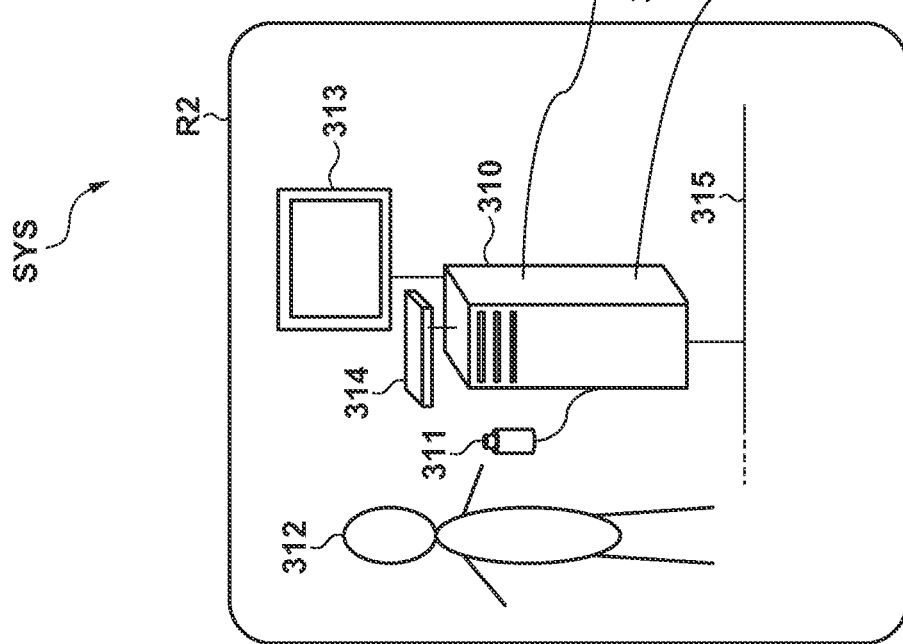

RADIATION IMAGING SYSTEM, RADIATION IMAGING APPARATUS, CONTROL METHOD OF RADIATION IMAGING SYSTEM, AND NON-TRANSITORY COMPUTER-READABLE STORAGE MEDIUM

BACKGROUND

Field of the Disclosure

The present disclosure relates to a radiation imaging system, a radiation imaging apparatus, a control method of the radiation imaging system, and a non-transitory computer-readable storage medium.

Description of the Related Art

For medical image diagnosis and nondestructive inspection, a radiation imaging apparatus using a sensor which detects radiation has been broadly used. It is known that, in such a radiation imaging apparatus, radiation entering the radiation imaging apparatus is monitored to detect the start and end of radiation irradiation and the integrated irradiation amount of radiation. Japanese Patent Laid-Open No. 2017-094007 discloses a radiation imaging system in which a radiation imaging apparatus and a generation controller, which controls irradiation of radiation from a radiation source, perform wireless communication to control radiation irradiation.

The communication environment is influenced by the external environment, the operation status in the radiation imaging apparatus, and the like. Japanese Patent Laid-Open No. 2017-094007 describes that the relatively stable frequency band is selected using a communication environment parameter such as an RSSI (Received Signal Strength Indicator) to perform communication between the radiation imaging apparatus and the generation controller.

SUMMARY

However, the RSSI may not have correlation with the actual communication time (communication speed). Then, it may take a longer time than expected for the signal transmitted from the radiation imaging apparatus to the generation controller to reach the generation controller, and this can decrease the controllability of radiation irradiation. Some embodiments of the present disclosure provide a technique advantageous in improving the controllability of radiation irradiation in a radiation imaging system.

According to some embodiments, a radiation imaging system comprising a radiation imaging apparatus configured to detect radiation emitted from a radiation source, an irradiation control apparatus configured to control the radiation source, a communication control apparatus configured to perform communication between the radiation imaging apparatus and the irradiation control apparatus, and a controller, wherein the radiation imaging apparatus is configured to communicate with the communication control apparatus in accordance with a setting selected from a plurality of settings by the controller, and the controller is configured to acquire a communication time for a predetermined communication amount between the radiation imaging apparatus and the communication control apparatus, and switch, in accordance with the communication time, the setting for communication of the radiation imaging apparatus with the communication control apparatus from a currently selected setting to another setting among the plurality of settings, is provided.

According to some other embodiments, a radiation imaging apparatus that communicates with an irradiation control apparatus, which controls a radiation source, via a communication control apparatus, wherein the radiation imaging apparatus is configured to communicate with the communication control apparatus in accordance with a setting selected from a plurality of settings, acquire a communication time for a predetermined communication amount between the radiation imaging apparatus and the communication control apparatus, and switch the setting for communication with the communication control apparatus from a currently selected setting to another setting among the plurality of settings in accordance with the communication time, is provided.

According to still other embodiments, a control method of a radiation imaging system comprising a radiation imaging apparatus configured to detect radiation emitted from a radiation source, an irradiation control apparatus configured to control the radiation source, and a communication control apparatus configured to perform communication between the radiation imaging apparatus and the irradiation control apparatus, wherein the radiation imaging apparatus is configured to communicate with the communication control apparatus in accordance with a setting selected from a plurality of settings, and the method comprises acquiring a communication time for a predetermined communication amount between the radiation imaging apparatus and the communication control apparatus, and switching, in accordance with the communication time, the setting for communication of the radiation imaging apparatus with the communication control apparatus from a currently selected setting to another setting among the plurality of settings, is provided.

According to yet other embodiments, a non-transitory computer-readable storage medium storing a program for causing a computer to execute a control method of a radiation imaging system comprising a radiation imaging apparatus configured to detect radiation emitted from a radiation source, an irradiation control apparatus configured to control the radiation source, and a communication control apparatus configured to perform communication between the radiation imaging apparatus and the irradiation control apparatus, wherein the radiation imaging apparatus is configured to communicate with the communication control apparatus in accordance with a setting selected from a plurality of settings, and the method comprises acquiring a communication time for a predetermined communication amount between the radiation imaging apparatus and the communication control apparatus, and switching, in accordance with the communication time, the setting for communication of the radiation imaging apparatus with the communication control apparatus from a currently selected setting to another setting among the plurality of settings, is provided.

Further features of various embodiments will become apparent from the following description of exemplary embodiments (with reference to the attached drawings).

BRIEF DESCRIPTION OF THE DRAWINGS

FIG. 1 is a view showing a configuration example of a radiation imaging system according to an embodiment;

DESCRIPTION OF THE EMBODIMENTS

Figure 2:
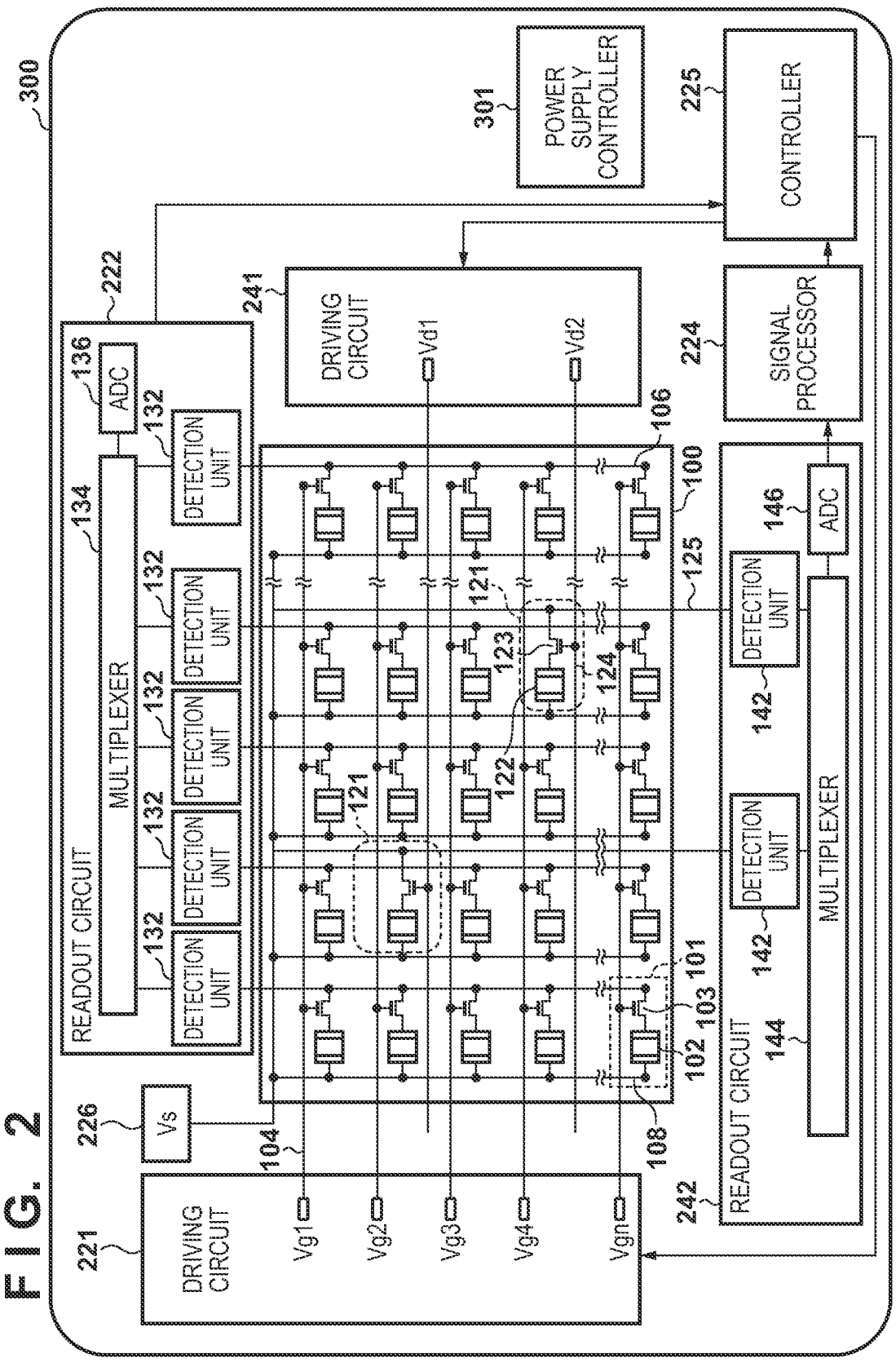
FIG. 2 is a view showing an arrangement example of a radiation imaging apparatus used in the radiation imaging system shown in FIG. 1.

Hereinafter, embodiments will be described in detail with reference to the attached drawings. Note, the following embodiments are not intended to limit the scope of the claims. Multiple features are described in the embodiments, but limitation is not made to embodiments that require all such features, and multiple such features may be combined as appropriate. Furthermore, in the attached drawings, the same reference numerals are given to the same or similar configurations, and redundant description thereof is omitted.

Radiation in the present disclosure can include α-rays, β-rays, γ-rays, and the like, which are beams generated by particles (including photons) emitted by radiation decay, as well as beams having the similar or higher energy, for example, X-rays, particle beams, cosmic rays, and the like.

With reference to FIGS. 1 to 6, a radiation imaging system according to this embodiment will be described. FIG. 1 is a view showing a configuration example of a radiation imaging system SYS in this embodiment. As shown in FIG. 1, the radiation imaging system SYS is provided in a radiation room R1 in which radiation imaging by radiation irradiation is performed and a control room R2 installed in the vicinity of the radiation room R1. However, some embodiments are not limited to this, and a component constituting the radiation imaging system SYS may be arranged in a room other than the radiation room R1 and the control room R2.

In the radiation room R1, as the components of the radiation imaging system SYS, a radiation imaging apparatus 300, an access point 320, a communication control apparatus 323, an irradiation control apparatus 324, and a radiation source 325 are arranged. Further, an entry apparatus 322, an AP communication cable 326, a radiation generation apparatus communication cable 327, and a sensor communication cable 328 are arranged in the radiation room R1. In the control room R2, as the components of the radiation imaging system SYS, a control apparatus 310, a radiation irradiation switch 311, a display apparatus 313, an input apparatus 314, an in-hospital LAN 315, and radiation room communication cables 316 are provided.

The radiation imaging apparatus 300 detects the radiation emitted from the radiation source 325. The radiation imaging apparatus 300 includes a power supply controller 301 formed by a battery or the like, a short-distance wireless communication unit 302, a registration switch 303, a wireless communication unit 304, and a wired communication unit 306. The radiation imaging apparatus 300 detects radiation transmitted through a subject 307 and generates radiation image data.

The access point 320 is an access point for performing wireless communication and is used for communication between the radiation imaging apparatus 300 and the control apparatus 310 via the communication control apparatus 323.

The communication between the radiation imaging apparatus 300 and the communication control apparatus 323 can be wired communication using the sensor communication cable 328. The access point 320 communicates with the radiation imaging apparatus 300 using, for example, the 2.4 GHz band, 5 GHz band, 6 GHz band, or the like of the wireless LAN.

The irradiation control apparatus 324 controls the radiation source 325 to irradiate the subject 307 with radiation. The irradiation control apparatus 324 can include a radiation source controller that controls the radiation source 325 so as to emit radiation based on a predetermined condition set by an operator 312 (for example, radiologist). The irradiation control apparatus 324 can also include a generation controller that controls the radiation source 325 to emit or stop radiation based on a signal indicating the start or stop of radiation irradiation output from the radiation imaging apparatus 300. Communication between the radiation imaging apparatus 300 and the irradiation control apparatus 324 is performed via the above-described communication control apparatus 323. As the irradiation control apparatus 324, the radiation source controller and the generation controller may be integrally formed, or may be separately formed.

The AP communication cable 326 is a cable for connecting the access point 320 and the communication control apparatus 323. The radiation generation apparatus communication cable 327 is a cable for connecting the irradiation control apparatus 324 and the communication control apparatus 323.

The control apparatus 310 communicates with the irradiation control apparatus 324 and the radiation imaging apparatus 300 via the communication control apparatus 323, the access point 320, the sensor communication cable 328, and the like. The control apparatus 310 comprehensively controls the radiation imaging system SYS in accordance with an order of the operator 312.

The radiation irradiation switch 311 inputs a timing of radiation irradiation in accordance with an operation of the operator 312. The input apparatus 314 is an apparatus used by the operator 312 to input a radiation imaging order. Various input devices, such as a keyboard and touch panel, are used for the input apparatus 314. The display apparatus 313 displays radiation image data having undergone image processing, a GUI, and the like. A display or the like can be used for the display apparatus 313. The in-hospital LAN 315 is an in-hospital backbone network. For example, pieces of information, such as the radiation imaging portion of the subject 307 and the imaging condition, are transmitted from a doctor via the in-hospital LAN 315. The radiation room communication cables 316 are cables for connecting the control apparatus 310 arranged in the control room R2 with the communication control apparatus 323 and the entry apparatus 322 arranged in the radiation room R1.

Next, an operation of the radiation imaging system SYS will be described. First, the operator 312 registers the radiation imaging apparatus 300 to the radiation imaging system SYS. When the registration switch 303 of the radiation imaging apparatus 300 is pressed by the operator 312, short-distance wireless communication is started between the short-distance wireless communication unit 302 of the radiation imaging apparatus 300 and the entry apparatus 322.

The control apparatus 310 transmits wireless connection related information of the access point 320 to the radiation imaging apparatus 300 via the short-distance wireless communication of the entry apparatus 322. The wireless connection related information includes, for example, a communication method such as IEEE802.11, a physical channel, an SSID, an encryption key, and the like in a case of a wireless LAN.

The radiation imaging apparatus 300 performs setting of the wireless communication unit 304 in accordance with the received wireless LAN connection related information. With this setting, the radiation imaging apparatus 300 establishes a wireless communication connection between the access point 320 and the wireless communication unit 304.

Then, the operator 312 inputs, to the control apparatus 310, subject information, such as the ID, name, and date of birth of the subject 307, and the imaging portion of the subject 307. These pieces of information may be transmitted to the control apparatus 310 via the in-hospital LAN 315, and the operator 312 may select the appropriate information. After inputting the information, such as the imaging portion, to the control apparatus 310, the operator 312 fixes the posture of the subject 307 and fixes the positional relationship among the subject 307, the radiation imaging apparatus 300, and the radiation source 325.

When the preparation for imaging is completed, the operator 312 presses the radiation irradiation switch 311. When the radiation irradiation switch 311 is pressed, radiation is emitted from the radiation source 325 toward the subject 307.

The radiation imaging apparatus 300 performs wireless communication with the irradiation control apparatus 324 to control the start and end of radiation irradiation. The radiation emitted toward the subject 307 is transmitted through the subject 307 and enters the radiation imaging apparatus 300. The radiation imaging apparatus 300 converts the incident radiation into visible light, and then detects it as a radiation image signal by a photoelectric conversion element.

The radiation imaging apparatus 300 drives the photoelectric conversion element to read out the radiation image signal and converts the analog signal into a digital signal by an AD conversion circuit, thereby obtaining digital radiation image data. The obtained digital radiation image data is transferred from the radiation imaging apparatus 300 to the control apparatus 310 by wireless communication.

The control apparatus 310 performs image processing on the received digital radiation image data. The control apparatus 310 causes the display apparatus 313 to display a radiation image based on the image-processed radiation image data. In this case, the control apparatus 310 functions as an image processing apparatus and a display control apparatus.

FIG. 2 is a view showing an arrangement example of the radiation imaging apparatus 300. As shown in FIG. 2, the radiation imaging apparatus 300 includes a radiation detector 100. The radiation detector 100 has a function of detecting emitted radiation. The radiation detector 100 includes a plurality of pixels arranged so as to form a plurality of rows and a plurality of columns. In the following description, a region in the radiation detector 100 where the plurality of pixels are arranged may be referred to as an imaging region. The plurality of pixels include a plurality of imaging pixels 101 for acquiring a radiation image, and one or more detection pixels 121 for monitoring irradiation of radiation. A plurality of the detection pixels 121 may be arranged in the imaging region of the radiation detector 100.

The imaging pixel 101 includes a conversion element 102 that converts radiation into an electrical signal, and a switch element 103 arranged between a column signal line 106 and the conversion element 102. The detection pixel 121 includes a conversion element 122 that converts radiation into an electrical signal, and a switch element 123 arranged between a detection signal line 125 and the conversion element 122. The detection pixel 121 is arranged in the same column as some of the plurality of imaging pixels 101.

Each of the conversion element 102 and the conversion element 122 can be formed by a scintillator that converts radiation into light and a photoelectric conversion element that converts light into an electrical signal. The scintillator is generally formed in a sheet shape so as to cover the imaging region, and is shared by the plurality of pixels. Each of the conversion element 102 and the conversion element 122 may be formed by a conversion element that directly converts radiation into light. Each of the switch element 103 and the switch element 123 may be, for example, a thin film transistor (TFT) with an active region formed by a semiconductor such as amorphous silicon or polysilicon. The detection pixel 121 may have the same structure as the imaging pixel 101. That is, the conversion element 102 and the conversion element 122 may have the same structure, and the switch element 103 and the switch element 123 may have the same structure.

The radiation imaging apparatus 300 includes a plurality of the column signal lines 106 and a plurality of driving lines 104. Each column signal line 106 corresponds to one of the plurality of columns in the imaging region. Each driving line 104 corresponds to one of the plurality of rows in the imaging region. Each driving line 104 is driven by a driving circuit 221.

One electrode of the main electrodes of the conversion element 102 is connected to one electrode of the main electrodes of the switch element 103, and the other electrode of the main electrodes of the conversion element 102 is connected to a bias line 108. Each bias line 108 extends in the column direction so as to correspond to each column of the plurality of pixels, and is commonly connected to the other electrodes of the main electrodes of the multiple conversion elements 102 arranged in the column direction. A bias voltage Vs is supplied to the bias line 108 from an element power supply circuit 226.

The power supply controller 301 is formed by including a battery, a DC-DC converter, and the like. The power supply controller 301 includes the element power supply circuit 226, and generates a power supply for an analog circuit and a power supply for a digital circuit that performs drive control, wireless communication, and the like.

The other electrodes of the main electrodes of the switch elements 103 of the multiple imaging pixels 101 forming one column are connected to one column signal line 106. The control electrodes of the switch elements 103 of the multiple imaging pixels 101 forming one row are connected to one driving line 104. Each column signal line 106 is connected to a readout circuit 222. Here, the readout circuit 222 includes a plurality of detection units 132, a multiplexer 134, and an analog/digital converter (AD converter) 136.

Each of the plurality of column signal lines 106 is connected to the corresponding detection unit 132 among the plurality of detection units 132 of the readout circuit 222. One column signal line 106 corresponds to one detection unit 132. The detection unit 132 includes, for example, a differential amplifier. The multiplexer 134 selects the plurality of detection units 132 in a predetermined order, and supplies a signal output from the selected detection unit 132 to the AD converter 136. The AD converter 136 converts the supplied signal into a digital signal and outputs the digital signal.

One electrode of the main electrodes of the conversion element 122 is connected to one electrode of the main electrodes of the switch element 123, and the other electrode of the main electrodes of the conversion element 122 is connected to the bias line 108. The other electrode of the main electrodes of the switch element 123 is connected to the detection signal line 125. The control electrode of the switch element 123 is electrically connected to a driving line 124.

The radiation imaging apparatus 300 can include a plurality of the detection signal lines 125. One or more detection pixels 121 are connected to one detection signal line 125. The driving line 124 is driven by a driving circuit 241. One or more detection pixels 121 are connected to one driving line 124. The detection signal line 125 is connected to a readout circuit 242. The readout circuit 242 includes a plurality of detection units 142, a multiplexer 144, and an AD converter 146.

Each of the plurality of detection signal lines 125 is connected to the corresponding detection unit 142 among the plurality of detection units 142 of the readout circuit 242. One detection signal line 125 corresponds to one detection unit 142. The detection unit 142 includes, for example, a differential amplifier. The multiplexer 144 selects the plurality of detection units 142 in a predetermined order, and supplies a signal output from the selected detection unit 142 to the AD converter 146. The AD converter 146 converts the supplied signal into a digital signal and outputs the digital signal.

The output of the readout circuit 242 (AD converter 146) is supplied to a signal processor 224 and processed by the signal processor 224. The signal processor 224 may output information indicating radiation irradiation with respect to the radiation imaging apparatus 300 based on the output of the readout circuit 242 (AD converter 146). More specifically, for example, the signal processor 224 may detect radiation irradiation with respect to the radiation imaging apparatus 300, or the signal processor 224 may calculate the irradiation amount and/or integrated irradiation amount of radiation.

A controller 225 controls the operation of the radiation imaging apparatus 300. More specifically, the controller 225 controls the driving circuit 221, the driving circuit 241, the readout circuits 222 and 242, and the like based on information from the signal processor 224 and a control command from the control apparatus 310. The controller 225 may be arranged in the radiation imaging apparatus 300 as shown in FIG. 2, or may be arranged separately from the radiation imaging apparatus 300. Any form may be used as long as the operation of the radiation imaging apparatus 300 to be described later can be controlled.

Next, the dose control operation of the radiation imaging system SYS using the radiation imaging apparatus 300 will be described. The operator 312 inputs the radiation irradiation conditions, such as the radiation irradiation dose, the maximum irradiation time, the tube current, and the tube voltage, the radiation detection region (ROI) where the radiation is to be monitored, the portion information, and the like to the control apparatus 310. The control apparatus 310 transmits the input radiation irradiation conditions, ROI, portion information, and the like to the radiation imaging apparatus 300 and the irradiation control apparatus 324. When the preparation for imaging is completed and the operator 312 presses the radiation irradiation switch 311, radiation is emitted from the radiation source 325 in accordance with the signal output from the irradiation control apparatus 324. The emitted radiation is transmitted through the subject 307 and enters the radiation imaging apparatus 300.

Based on the radiation irradiation stop timing transmitted from the control apparatus 310 and set, the radiation imaging apparatus 300 notifies the irradiation control apparatus 324 of the stop of radiation irradiation via the communication control apparatus 323 using wireless communication or the like. The irradiation control apparatus 324 causes the radiation source 325 to stop the radiation irradiation based on the notified radiation irradiation stop timing.

The radiation imaging apparatus 300 detects the radiation incident on the ROI by the detection pixel 121, and the signal processor 224 calculates an integrated irradiation amount, which is an integrated value of the doses (arrival doses) detected in a predetermined period. Here, the controller 225 calculates an appropriate dose from the integrated irradiation amount information supplied from the signal processor 224 and from the portion information and imaging conditions input by the operator 312, and the controller 225 decides a radiation irradiation stop timing. In this embodiment, the radiation imaging apparatus 300 notifies the stop of radiation irradiation as a result of detecting the radiation, but some embodiments are not limited to this. It may be configured such that the radiation imaging apparatus 300 transmits the arrival dose every predetermined time to the irradiation control apparatus 324 and the irradiation control apparatus 324 calculates the integrated value of the arrival doses. The radiation irradiation stop timing may be decided by the maximum irradiation time input to the control apparatus 310 by the operator 312.

Figure 3:
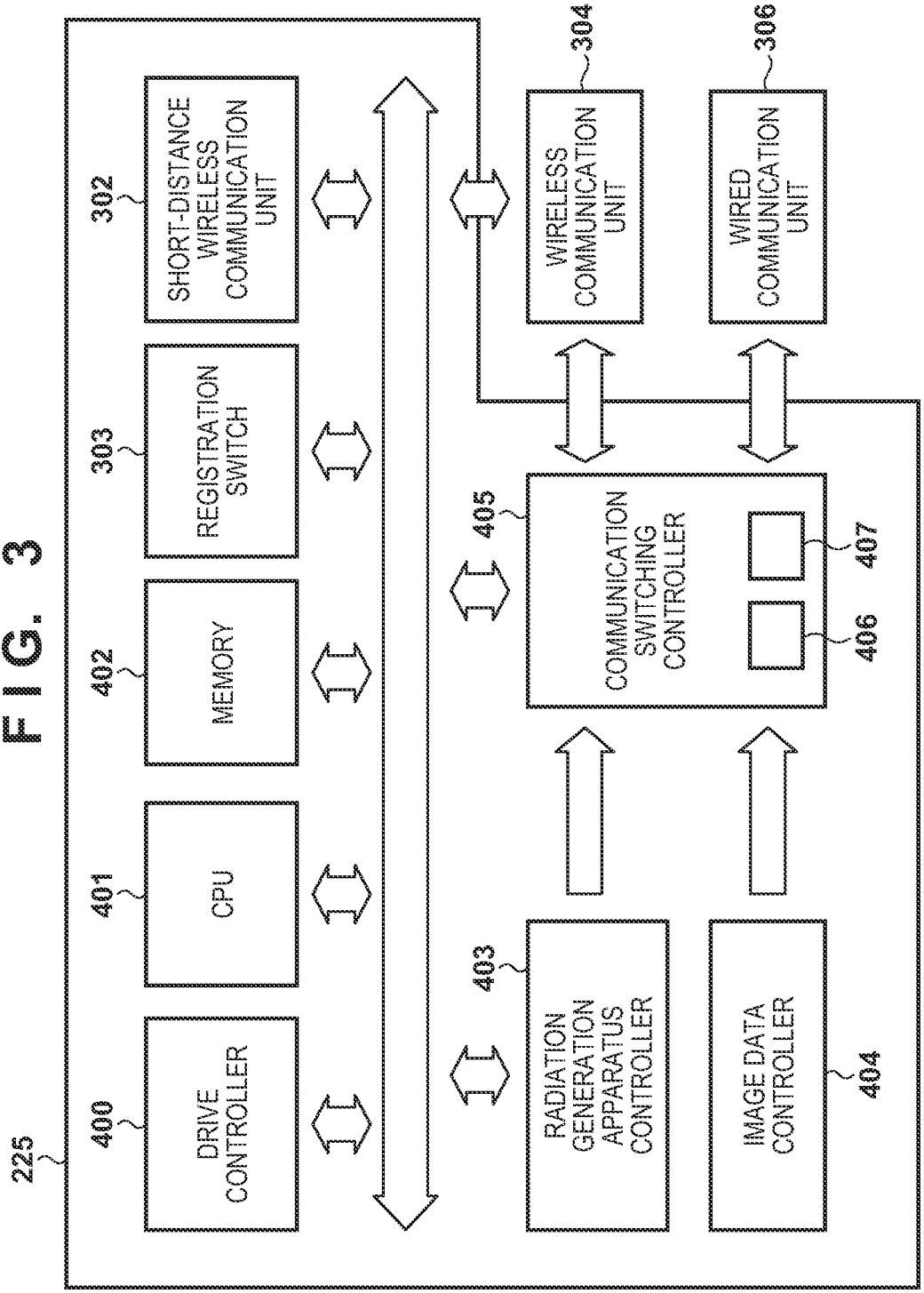
FIG. 3 is a block diagram showing an arrangement example of a controller used in the radiation imaging system shown in FIG. 1.

FIG. 3 is a block diagram showing the controller 225 of the radiation imaging apparatus 300. As shown in FIG. 3, the controller 225 includes a drive controller 400, a CPU 401, a memory 402, a radiation generation apparatus controller 403, and an image data controller 404. The controller 225 can further include a communication switching controller 405, the registration switch 303, the short-distance wireless communication unit 302, the wireless communication unit 304, and the wired communication unit 306.

The drive controller 400 controls the driving circuits 221 and 241 and the readout circuits 222 and 242 based on information input from the signal processor 224 and a command transmitted from the control apparatus 310. The CPU 401 controls the entire radiation imaging apparatus 300 using programs and various types of data stored in the memory 402. The memory 402 stores, for example, programs and various types of data used when the CPU 401 executes processing. Further, the memory 402 may store various types of data obtained from processing by the CPU 401, and radiation image data. The short-distance wireless communication unit 302 performs short-distance wireless communication with the entry apparatus 322. The registration switch 303 is a switch for starting short-distance wireless communication with the entry apparatus 322.

The communication switching controller 405 includes a communication time acquiring unit 406 that acquires the communication time in arbitrary communication, more specifically, information concerning the communication time in the communication having a predetermined communication amount (data amount), and a communication time determining unit 407 that compares the information concerning the communication time with an arbitrary reference value. The communication switching controller 405 controls switching of the connection with the communication control apparatus 323 between the wireless communication unit 304 and the wired communication unit 306.

The radiation imaging apparatus 300 is configured to communicate with the communication control apparatus 323 in accordance with the setting selected from a plurality of settings by the communication switching controller 405 of the controller 225. In the configuration shown in FIGS. 1 and 3, the radiation imaging apparatus 300 includes the wireless communication unit 304 and the wired communication unit 306 each used to communicate with the communication control apparatus 323. The communication switching controller 405 of the controller 225 acquires the communication time for a predetermined communication amount between the radiation imaging apparatus 300 and the communication control apparatus 323 and, in accordance with the communication time, switches the setting for communication of the radiation imaging apparatus 300 with the communication control apparatus 323 from the currently selected setting to another setting among the plurality of settings. In this specification, the communication time is, for example, a physical quantity using a unit such as [sec/packet] and indicating the time required for the communication having an arbitrary communication amount (data amount). Also, for example, the communication time acquiring unit 406 may acquire information concerning the communication speed (for example, the physical quantity using bps or the like as the unit and obtained by dividing the communication amount by the communication time) derived from the communication amount and the communication time in arbitrary communication, and the communication time determining unit 407 may compare the information concerning the communication speed with an arbitrary reference value.

For example, when the radiation imaging apparatus 300 performs communication using the wireless communication unit 304, the wireless communication unit 304 communicates with the communication control apparatus 323 via the access point 320. For example, the wireless communication unit 304 performs communication of a signal having a predetermined communication amount with the communication control apparatus 323, and outputs the information concerning the communication time to the communication time acquiring unit 406. The wireless communication unit 304 may communicate with the communication control apparatus 323 a plurality of times, and the communication time acquiring unit 406 may acquire, for example, information, such as the maximum value, average value, standard deviation, or the like, of the communication times. Here, the signal having the predetermined communication amount may be a test signal used to check the communication circumstance between the radiation imaging apparatus 300 and the communication control apparatus 323. Also, for example, the communication having the predetermined communication amount may be of a signal, such as the information concerning an exposure control function (to be described later), which is used when actually performing imaging using the radiation imaging system SYS.

The communication time acquiring unit 406 acquires the communication time between the radiation imaging apparatus 300 and the communication control apparatus 323 from the wireless communication unit 304. The communication time may be the time from transmission of the signal having the predetermined communication amount from the radiation imaging apparatus 300 using the wireless communication unit 304 or the wired communication unit 306 to the communication control apparatus 323 to reception of a signal output from the communication control apparatus 323 and indicating that the signal having the predetermined communication amount has been received. Also, for example, a common counting system in the radiation imaging system SYS may count, as the communication time, the time from output of the signal having the predetermined communication amount by the radiation imaging apparatus 300 to reception of the signal by the communication control apparatus 323.

Then, the communication time determining unit 407 compares the information of the communication time with the predetermined reference value, and determines whether the communication time satisfies the reference value. For example, the communication time acquiring unit 406 of the controller 225 acquires the communication time according to the currently selected setting among the plurality of settings a plurality of times, and the communication time determining unit 407 determines whether at least one of the maximum value of the plurality of communication times, the average value of the plurality of communication times, or the standard deviation of the plurality of communication times satisfies the predetermined reference value. If it is determined that the communication time does not satisfy the reference value, the communication switching controller 405 switches the setting for communication of the radiation imaging apparatus 300 with the communication control apparatus 323 from the setting for using the wireless communication unit 304 to the setting for using the wired communication unit 306. Switching of the communication setting is not limited to the above-described example, but the communication setting may be switched from the setting for using the wired communication unit 306 to the setting for using the wireless communication unit 304.

As has been described above, in accordance with the communication time for the signal having the predetermined communication amount between the radiation imaging apparatus 300 and the communication control apparatus 323, the setting for communication of the radiation imaging apparatus 300 with the communication control apparatus 323 is switched from the currently selected setting to another setting among the plurality of settings. As compared to a case of switching the method used for communication in accordance with the signal strength or the like, using the actual communication time corresponding to the communication amount enables control more suitable for the circumstance where the radiation imaging system SYS is arranged, such as the influence of noise caused by another apparatus. That is, the controllability of radiation irradiation in the radiation imaging system SYS is improved.

Figure 4:
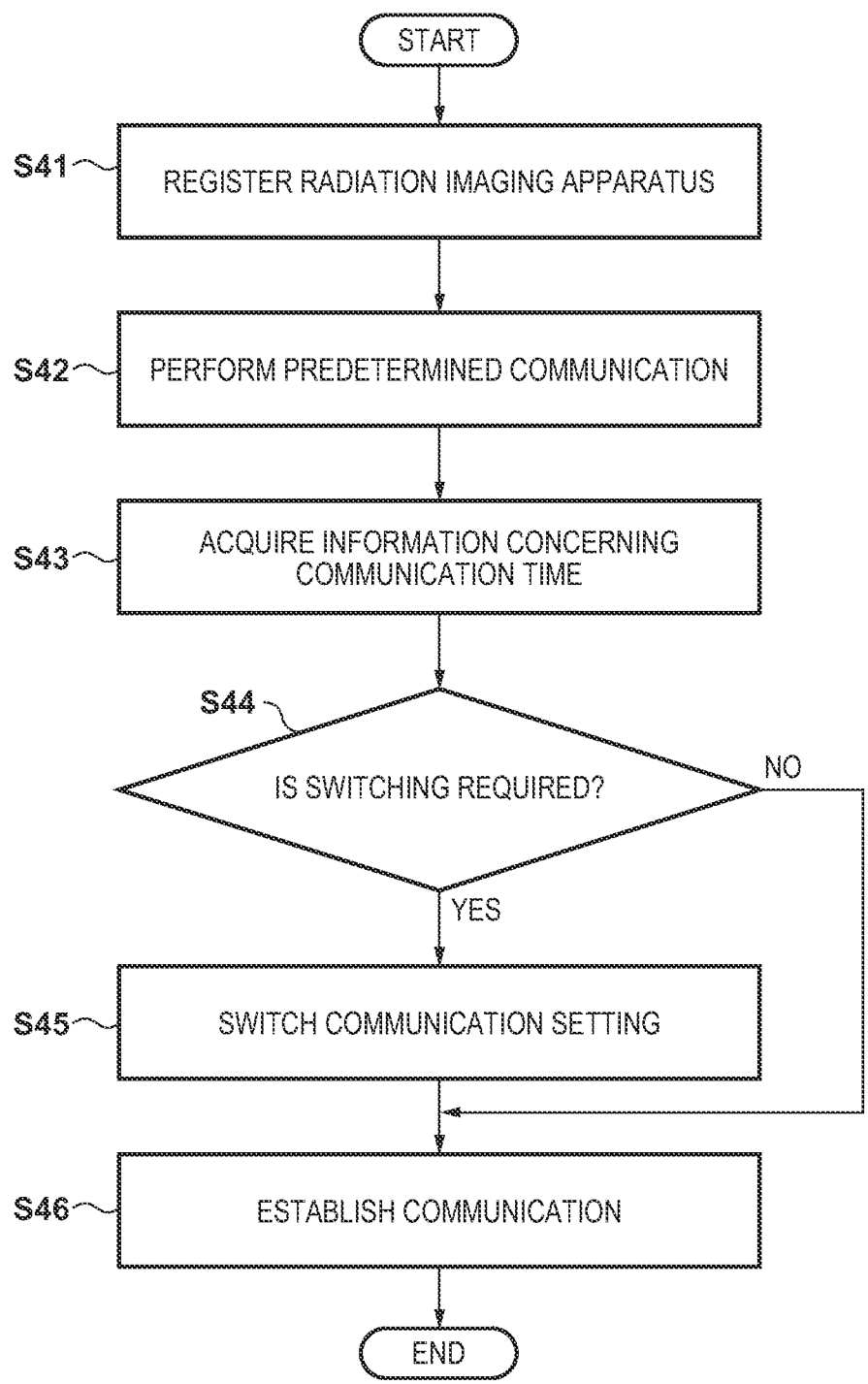
FIG. 4 is a flowchart illustrating the communication setting switching operation in the radiation imaging system shown in FIG. 1.

With reference to the flowchart of FIG. 4, the switching operation of switching the setting for communication of the radiation imaging apparatus 300 with the communication control apparatus 323 will be described. When the radiation imaging apparatus 300 is activated, in step S41, the operator 312 registers the radiation imaging apparatus 300 to the radiation imaging system SYS, as has been described above.

If the radiation imaging apparatus 300 is registered to the radiation imaging system SYS, in step S42, the communication unit of the wireless communication unit 304 and the wired communication unit 306 which is currently set in the radiation imaging apparatus 300 performs predetermined communication with the communication control apparatus 323. Then, in step S43, the communication time acquiring unit 406 acquires the information concerning the communication time for a predetermined communication amount. For example, the information concerning the communication time may be the information such as the maximum value, an average value, a standard deviation, or the like of the communication times of the communication performed a plurality of times. Also, the information concerning the communication time may be a combination including at least two of the following: the maximum value of the communication times, an average value of the communication times, a standard deviation of the communication times, or the like of the communication times.

If the communication time between the radiation imaging apparatus 300 and the communication control apparatus 323 is acquired, in step S44, the communication time determining unit 407 compares the information concerning the communication time acquired in step S43 with a predetermined reference value. The reference value may be decided based on the radiation imaging procedure or the driving method of the radiation imaging apparatus 300, or the reference value may be decided based on the radiation irradiation conditions, such as the radiation dose, the maximum irradiation time, the tube current, and the tube voltage, the ROI, the portion information, and the like input to the control apparatus 310 by the operator 312. For example, the reference value may be supplied from the control apparatus 310 together with the irradiation conditions, the ROI, the portion information, and the like. It may be configured such that combinations each including the irradiation conditions, the ROI, the portion information, the reference value, and the like are stored in the control apparatus 310 in correspondence with a plurality of radiation imaging procedures, and the operator 312 appropriately selects one of the combinations.

If the information concerning the communication time is compared with the predetermined reference value, and the communication time determining unit 407 determines that the information concerning the communication time satisfies the reference value, after it is confirmed in step S46 that the radiation imaging apparatus 300 and the communication control apparatus 323 can communicate each other using the currently selected communication unit (the wireless communication unit 304 or the wired communication unit 306), the switching processing is terminated. If the communication time determining unit 407 determines that the information concerning the communication time does not satisfy the reference value, the process advances to step S45.

In step S45, based on the determination result in step S44, the communication switching controller 405 switches the setting for communication of the radiation imaging apparatus 300 with the communication control apparatus 323. Here, a case will be described in which the currently selected communication unit is the wireless communication unit 304. In this case, the communication switching controller 405 switches the setting for communication of the radiation imaging apparatus 300 with the communication control apparatus 323 from the setting for using the wireless communication unit 304 to the setting for using the wired communication unit 306. With this operation, the radiation imaging apparatus 300 uses the wired communication unit 306 for communication with the communication control apparatus 323 in accordance with the setting selected by the communication switching controller 405 of the controller 225. Then, after it is confirmed in step S46 that the radiation imaging apparatus 300 and the communication control apparatus 323 can communicate with each other using the selected wired communication unit 306, the switching processing is terminated.

In the embodiment described above, it has been described that the setting for communication of the radiation imaging apparatus 300 with the communication control apparatus 323 includes the setting for using the wireless communication unit 304 and the setting for using the wired communication unit 306, and the communication time of the currently selected communication unit is acquired to determine whether to switch the setting. However, some embodiments are not limited to this.

For example, the communication time acquiring unit 406 of the controller 225 may acquire the communication times of the plurality of settings. In this case, the communication switching controller 405 of the controller 225 may switch the setting for communication of the radiation imaging apparatus 300 with the communication control apparatus 323 to the setting with the shortest communication time among the plurality of settings. For example, communication of the signal having the predetermined communication amount is performed, and the shortest communication time in a case of using the wireless communication unit 304 and the shortest communication time in a case of using the wired communication unit 306 are acquired, and the communication unit with the shorter communication time may be selected for communication with the communication control apparatus 323.

Further, in this embodiment, the example has been described in which the wireless communication unit 304 uses the 2.4 GHz band, the 5 GHz band, and the 6 GHz band, but some embodiments are not limited to this, and another frequency band may be used. In addition, in this embodiment, IEEE802.11 has been described as the example of the communication method, but some embodiments are not limited to this, and another communication method may be used.

Figure 5:
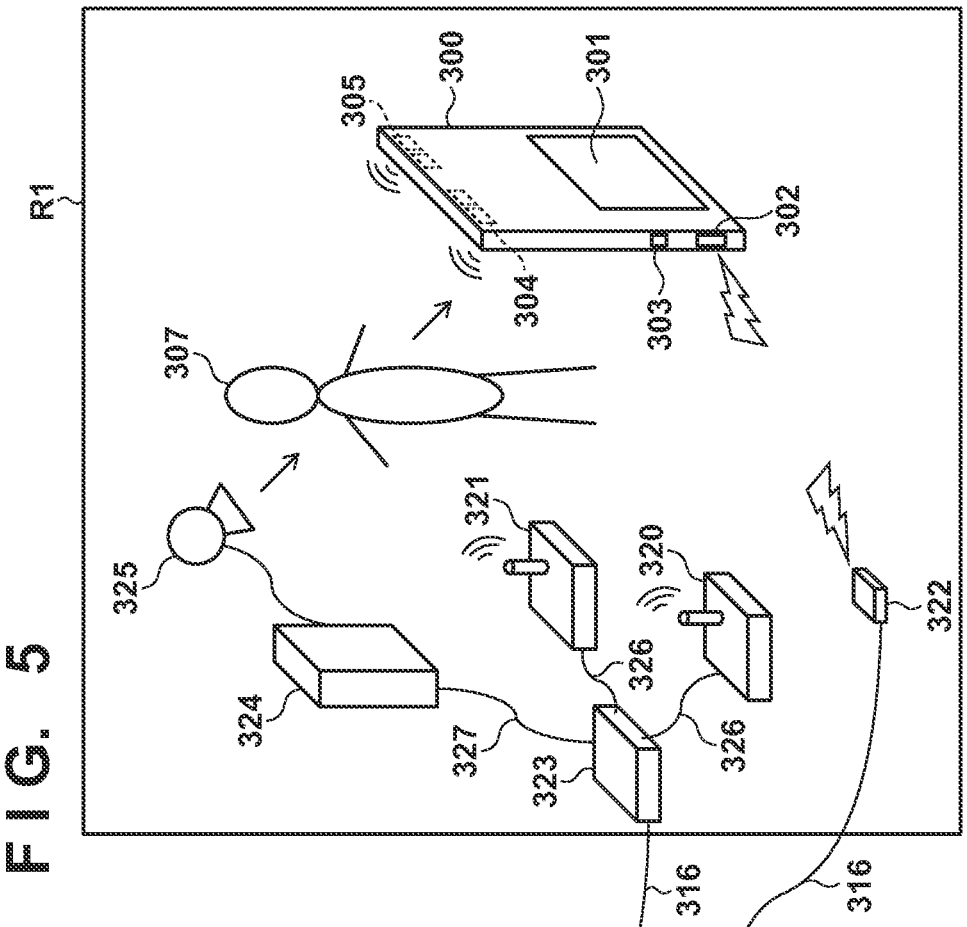
FIG. 5 is a view showing a modification of the radiation imaging system shown in FIG. 1.
Figure 6:
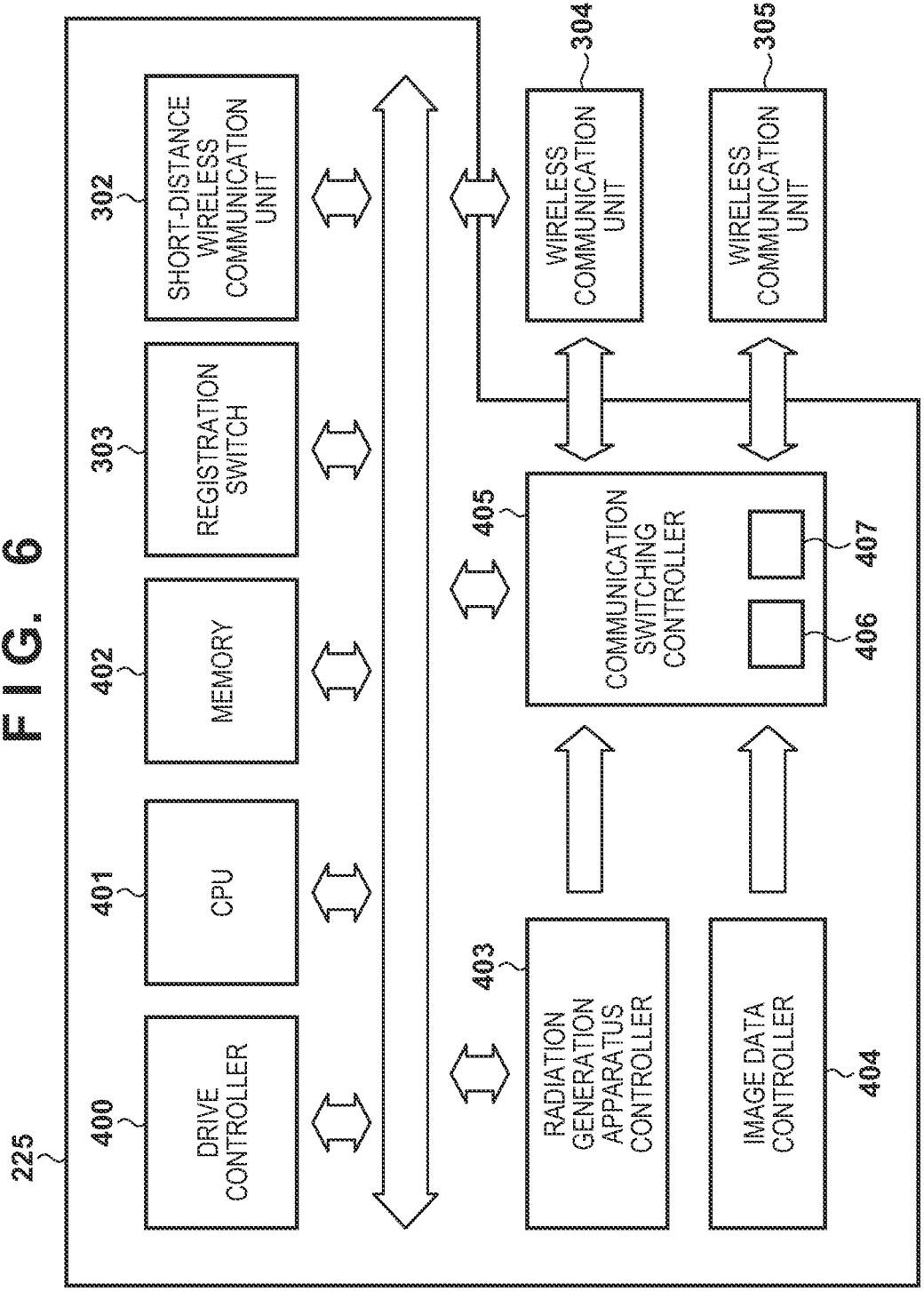
FIG. 6 is a block diagram showing a modification of the controller shown in FIG. 2.

In the embodiment described above, the case has been described in which the setting for communication of the radiation imaging apparatus 300 with the communication control apparatus 323 includes the setting for using the wireless communication unit 304 and the setting for using the wired communication unit 306. However, some embodiments are not limited to this, and as shown in FIGS. 5 and 6, the radiation imaging apparatus 300 may include a plurality of wireless communication units including the wireless communication unit 304 and a wireless communication unit 305 used to communicate with the communication control apparatus 323. In this case, the procedure of a switching operation upon switching the setting for communication of the radiation imaging apparatus 300 with the communication control apparatus 323 may be similar to that described using FIG. 4. Here, differences in steps shown in FIG. 4 from the above-described embodiment will be described.

The access point 320 for connection with the wireless communication unit 304 of the radiation imaging apparatus 300 and an access point 321 for connection with the wireless communication unit 305 of the radiation imaging apparatus 300 are arranged in the radiation room R1. The radiation imaging apparatus 300 selects, from a plurality of settings for using respective wireless communication units of the plurality of wireless communication units 304 and 305, the wireless communication unit 304 or the wireless communication unit 305 in accordance with the wireless LAN connection related information received from the control apparatus 310 upon registration of the radiation imaging apparatus 300 to the radiation imaging system SYS. With this operation, the radiation imaging apparatus 300 can establish a wireless communication connection between the access point 320 and the wireless communication unit 304 or a wireless communication connection between the access points 321 and the wireless communication unit 305 (step S41).

In step S45, based on the determination result in step S44, the communication switching controller 405 switches the communication unit used by the radiation imaging apparatus 300. For example, if the currently selected communication unit is the wireless communication unit 304, and the communication time for the predetermined communication amount does not satisfy the predetermined reference value, the communication switching controller 405 switches the setting for communication of the radiation imaging apparatus 300 with the communication control apparatus 323, and controls the wireless communication unit 305 to perform communication with the communication control apparatus 323.

Here, the arrangement in which the radiation imaging apparatus 300 includes two wireless communication units 304 and 305 has been described as an example, but some embodiments are not limited to this. The radiation imaging apparatus 300 may include three or more wireless communication units, and the communication switching controller 405 of the controller 225 may select, from the three or more wireless communication units, the communication unit to communicate with the communication control apparatus 323. Further, for example, when the wired communication unit 306 is used to perform communication, the communication switching controller 405 may switch the setting for communication of the radiation imaging apparatus 300 with the communication control apparatus 323 to the setting for using one of the plurality of wireless communication units.

For example, the plurality of settings for communication of the radiation imaging apparatus 300 with the communication control apparatus 323 may include settings for a plurality of output electric energies upon communication performed by the wireless communication unit 304. For example, when the wireless communication unit 304 is in use, if it is determined that the communication time for the predetermined communication amount does not satisfy the predetermined reference value, the electric energy of the communication wave output by the wireless communication unit 304 may be increased.

For example, the wireless communication unit 304 may be configured to communicate with the communication control apparatus 323 using a plurality of communication methods. In this case, the plurality of settings for communication of the radiation imaging apparatus 300 with the communication control apparatus 323 may include the settings for using respective communication methods of the plurality of communication methods. For example, when the wireless communication unit 304 is in use, if it is determined that the communication time for the predetermined communication amount does not satisfy the predetermined reference value, the used frequency band may be switched (for example, from the 2.4 GHz band to the 5 GHz band), or the compliant communication standard may be switched (for example, from IEEE802.11 to IEEE802.15).

For example, the communication control apparatus 323 may include a plurality of communication units (for example, the access points 320 and 321) capable of communication with the wireless communication unit 304. In this case, the plurality of settings for communication of the radiation imaging apparatus 300 with the communication control apparatus 323 may include the settings for using respective communication units of the plurality of communication units (for example, the access points 320 and 321). For example, when the wireless communication unit 304 is in use to perform wireless communication with the access point 320, if it is determined that the communication time for the predetermined communication amount does not satisfy the predetermined reference value, the connection between the wireless communication unit 304 and the access point 320 may be disconnected and the wireless communication unit 304 may be set to connect to the access point 321.

Next, control in a case in which the above-described radiation imaging system SYS has an exposure control function will be described. Here, the exposure control function can include control for acquiring the radiation dose (integrated dose) entering the radiation imaging apparatus 300 and stopping the irradiation of radiation from the radiation source 325. Also in this case, the procedure of a switching operation upon switching the setting for communication of the radiation imaging apparatus 300 with the communication control apparatus 323 may be similar to that described using FIG. 4. Here, differences in steps shown FIG. 4 from the above-described embodiment will be described.

The radiation imaging apparatus 300 detects the radiation entering the radiation detection region (ROI) by the detection pixel 121, and the signal processor 224 calculates the integrated irradiation amount which is the integrated value of the radiation doses (arrival doses) detected in a predetermined period. The controller 225 decides the radiation irradiation stop timing based on, for example, the irradiation conditions, such as the radiation irradiation dose input by the operator 312 before the radiation irradiation and supplied from the control apparatus 310 and the acquired integrated irradiation amount. Also, for example, the controller 225 may calculate the appropriate dose from the portion information, imaging conditions, and the like input by the operator 312, and decide the radiation irradiation stop timing from the integrated irradiation amount acquired by the signal processor 224.

After the radiation irradiation stop timing is decided, the radiation imaging apparatus 300 outputs a radiation irradiation stop signal to the communication control apparatus 323. If the radiation irradiation stop signal is received from the radiation imaging apparatus 300, the communication control apparatus 323 outputs the irradiation stop signal to the irradiation control apparatus 324. If the radiation irradiation stop signal is transferred, the irradiation control apparatus 324 controls the radiation source 325 to stop the radiation irradiation.

When using the exposure control function as described above, the communication time between the radiation imaging apparatus 300 and the communication control apparatus 323 may be acquired based on the time required to transmit information concerning the exposure control function from the radiation imaging apparatus 300 to the communication control apparatus 323. Here, let a time T1 be the time from decision of termination of the radiation irradiation by the radiation imaging apparatus 300 in accordance with the irradiated radiation dose to transmission of the irradiation stop signal to the communication control apparatus 323. Further, let a time T2 be the time from reception of the radiation irradiation stop signal by the communication control apparatus 323 to output of the irradiation stop signal to the irradiation control apparatus 324. Furthermore, let a time T3 be the time from reception of the irradiation stop signal from the communication control apparatus 323 by the irradiation control apparatus 324 to causing the radiation source 325 to stop the radiation irradiation. At this time, the predetermined reference value for switching the setting for communication of the radiation imaging apparatus 300 with the communication control apparatus 323 from the currently selected setting to another setting among the plurality of settings may be decided based on the time T1, the time T2, the time T3, and a nominal shortest irradiation time.

For example, with respect to a maximum value Tmax of the communication time for the information concerning the exposure control function having a predetermined communication amount (data amount), if the following inequality (1) is not satisfied, the controller 225 may operate so as to switch the setting for communication of the radiation imaging apparatus 300 with the communication control apparatus from the currently selected setting to another setting among the plurality of settings as described above.

$$Tmax < \alpha(Taec - T1 - T2 - T3) \quad (1)$$

where α is a predetermined coefficient, and Taec is a nominal shortest irradiation time.

Also, for example, communication may be performed a plurality of times using the currently selected communication unit, and the reference value may be decided according to inequality (2) using an average value Tave of the communication times. Also, for example, communication may be performed a plurality of times using the currently selected communication unit, and the reference value may be decided according to inequality (3) using a standard deviation Tsig of the communication times.

$$Tave < \beta(Taec - T1 - T2 - T3) \quad (2)$$

$$Tsig < \gamma(Taec - T1 - T2 - T3) \quad (3)$$

where β and γ are predetermined coefficients.

If the communication time for the information concerning the exposure control function does not satisfy at least one of the reference values described above, the controller 225 operates so as to switch the setting for communication of the radiation imaging apparatus 300 with the communication control apparatus 323. The reference value used by the controller 225 to determine switching of the communication setting may be obtained by appropriately combining inequalities (1) to (3).

When the radiation imaging system SYS has the exposure control function, the setting for communication of the radiation imaging apparatus 300 with the communication control apparatus 323 is switched in accordance with the communication time for the information concerning the exposure control function having the predetermined communication amount between the radiation imaging apparatus 300 and the communication control apparatus 323. As compared to a case of switching the method used for communication in accordance with the signal strength or the like, using the actual communication time corresponding to the communication amount enables control more suitable for the circumstance where the radiation imaging system SYS is arranged. With this, even in a case in which the correlation between the signal strength and the communication time is low due to the influence of noise caused by another communication apparatus or a medical device (for example, a microwave therapy device or the like), the controllability of exposure control (radiation irradiation) is improved. Also, as has been described above, the setting for communication of the radiation imaging apparatus 300 with the communication control apparatus 323 may be switched in accordance with the communication speed of the information concerning the exposure control function between the radiation imaging apparatus 300 and the communication control apparatus 323. Also in this case, the influence of external noise or the like is suppressed, and the controllability of exposure control (radiation irradiation) is improved.

Other Embodiments

Some embodiment(s) can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2021-171149, which was filed on Oct. 19, 2021 and which is hereby incorporated by reference herein in its entirety.

What is claimed is:

1. A radiation imaging system
including a radiation imaging apparatus configured to detect radiation emitted from a radiation source,
an irradiation control apparatus configured to control the radiation source, and
a communication control apparatus configured to perform communication between the radiation imaging apparatus and the irradiation control apparatus,
the radiation imaging system further comprising
one or more controllers configured to
acquire a communication time for a predetermined communication amount between the radiation imaging apparatus and the communication control apparatus, and
switch, in a case where the communication time of a currently selected setting among a plurality of settings does not satisfy a predetermined reference value, a setting for communication of the radiation imaging apparatus with the communication control apparatus from the currently selected setting to another setting among the plurality of settings.

2. The system according to claim 1, wherein
the controller is configured to acquire the communication time of the currently selected setting among the plurality of settings a plurality of times, and
if at least one of a maximum value of a plurality of the communication times, an average value of a plurality of the communication times, or a standard deviation of a plurality of the communication times does not satisfy a predetermined reference value, the controller is configured to switch the setting for communication of the radiation imaging apparatus with the communication control apparatus.

3. The system according to claim 1, wherein
the controller is configured to
acquire the communication time of each of the plurality of settings, and
switch the setting for communication of the radiation imaging apparatus with the communication control apparatus to a setting with a shortest communication time among the plurality of settings.

4. The system according to claim 1, wherein
the system is configured to have an exposure control function, and
the communication time is acquired based on a time required to transmit information concerning the exposure control function from the radiation imaging apparatus to the communication control apparatus.

5. The system according to claim 1, wherein
the system is configured to have an exposure control function,
the communication time is acquired based on a time required to transmit information concerning the exposure control function from the radiation imaging apparatus to the communication control apparatus, and
the predetermined reference value is decided based on a first time from decision of termination of radiation irradiation by the radiation imaging apparatus in accordance with an irradiated radiation dose to transmission of an irradiation stop signal to the communication control apparatus, a second time from reception of the irradiation stop signal by the communication control apparatus to output of the irradiation stop signal to the irradiation control apparatus, a third time from reception of the irradiation stop signal by the irradiation control apparatus to causing the radiation source to stop the radiation irradiation, and a nominal shortest irradiation time.

6. The system according to claim 5, wherein
the predetermined reference value is decided based on a time obtained by subtracting a sum of the first time, the second time, and the third time from the nominal shortest irradiation time.

7. The system according to claim 1, wherein
the radiation imaging apparatus comprises a wireless communication unit and a wired communication unit each used to communicate with the communication control apparatus, and
the plurality of settings comprise a setting for using the wireless communication unit and a setting for using the wired communication unit.

8. The system according to claim 1, wherein
the radiation imaging apparatus comprises a plurality of wireless communication units used to communication with the communication control apparatus, and
the plurality of settings include a setting for using each wireless communication unit of the plurality of wireless communication units.

9. The system according to claim 1, wherein
the radiation imaging apparatus comprises a wireless communication unit used to communicate with the communication control apparatus, and
the plurality of settings comprise settings for a plurality of output electric energies upon communication performed by the wireless communication unit.

10. The system according to claim 1, wherein
the radiation imaging apparatus comprises a wireless communication unit used to communicate with the communication control apparatus,
the wireless communication unit is configured to communicate with the communication control apparatus using a plurality of communication methods, and
the plurality of settings comprise settings for using respective communication methods of the plurality of communication methods.

11. The system according to claim 1, wherein
the radiation imaging apparatus comprises a wireless communication unit used to communicate with the communication control apparatus,
the communication control apparatus comprises a plurality of communication units configured to communicate with the wireless communication unit, and
the plurality of settings include a plurality of settings for using respective communication units of the plurality of communication units.

12. A radiation imaging apparatus that communicates with an irradiation control apparatus, which controls a radiation source, via a communication control apparatus, the radiation imaging apparatus comprising:
one or more memories; and
one or more processors that cooperate with the one or more memories to control the radiation imaging apparatus to
communicate with the communication control apparatus in accordance with a setting selected from a plurality of settings,
acquire a communication time for a predetermined communication amount between the radiation imaging apparatus and the communication control apparatus, and
switch, in a case where the communication time of a currently selected setting among the plurality of settings does not satisfy a predetermined reference value, a setting for communication with the communication control apparatus from the currently selected setting to another setting among the plurality of settings.

13. A control method of a radiation imaging system comprising a radiation imaging apparatus configured to detect radiation emitted from a radiation source, an irradiation control apparatus configured to control the radiation source, and a communication control apparatus configured to perform communication between the radiation imaging apparatus and the irradiation control apparatus, wherein
the radiation imaging apparatus is configured to communicate with the communication control apparatus in accordance with a setting selected from a plurality of settings,
the method comprising:
acquiring a communication time for a predetermined communication amount between the radiation imaging apparatus and the communication control apparatus, and
switching, in a case where the communication time of a currently selected setting among the plurality of settings does not satisfy a predetermined reference value, a setting for communication of the radiation imaging apparatus with the communication control apparatus from the currently selected setting to another setting among the plurality of settings.

14. A non-transitory computer-readable storage medium storing a program for causing a computer to execute a control method of a radiation imaging system comprising a radiation imaging apparatus configured to detect radiation emitted from a radiation source, an irradiation control apparatus configured to control the radiation source, and a communication control apparatus configured to perform communication between the radiation imaging apparatus and the irradiation control apparatus, wherein the radiation imaging apparatus is configured to communicate with the communication control apparatus in accordance with a setting selected from a plurality of settings, the method comprising:

acquiring a communication time for a predetermined communication amount between the radiation imaging apparatus and the communication control apparatus, and switching, in a case where the communication time of a currently selected setting among the plurality of settings does not satisfy a predetermined reference value, a setting for communication of the radiation imaging apparatus with the communication control apparatus from the currently selected setting to another setting among the plurality of settings.

15. A radiation imaging system including a radiation imaging apparatus configured to detect radiation emitted from a radiation source, an irradiation control apparatus configured to control the radiation source, and a communication control apparatus configured to perform communication between the radiation imaging apparatus and the irradiation control apparatus, the radiation imaging system further comprising one or more controllers configured to:

acquire a communication time for a predetermined communication amount between the radiation imaging apparatus and the communication control apparatus in advance of radiation imaging, wherein the predetermined communication amount is a communication amount necessary for operating an automatic exposure control (AEC) function.

* * * * *